United States Patent [19]

Nebe et al.

[11] Patent Number: 4,691,110
[45] Date of Patent: Sep. 1, 1987

[54] LASER SPECTRAL FLUOROMETER

[75] Inventors: Wolfgang Nebe; Jutta Reichel; Klaus Biehler, all of Jena; Hartmut Lucht, Altglienicke; Heinz Drommert, Berlin, all of German Democratic Rep.

[73] Assignee: Jenoptik Jena GmbH, Jena, German Democratic Rep.

[21] Appl. No.: 716,002

[22] Filed: Mar. 25, 1985

[30] Foreign Application Priority Data

May 2, 1984 [DD] German Democratic Rep. ............ WPG01J/2625764

[51] Int. Cl.$^4$ .................. F21V 9/16; G01N 21/64
[52] U.S. Cl. ............... 250/458.1; 250/461.1; 356/318
[58] Field of Search .......... 250/458.1, 461.1; 356/318, 319

[56] References Cited

U.S. PATENT DOCUMENTS

| 4,421,860 | 12/1983 | Elings et al. | 250/458.1 |
| 4,461,573 | 7/1984 | Lucht et al. | 250/458.1 |
| 4,490,040 | 12/1984 | Lucht et al. | 250/458.1 |
| 4,531,834 | 7/1985 | Nogami | 250/458.1 |

Primary Examiner—Janice A. Howell
Attorney, Agent, or Firm—Jordan and Hamburg

[57] ABSTRACT

In order to improve the sensitivity and the spectral resolution in measuring the luminescence of diverse sample materials, adapted optical imaging relationships at variable excitation output are provided for the different optical paths of the luminescence light emitted by the sample material. An excitation bundle of rays which can be stopped down and the central beam of the secondary beam which emanates from the sample material, are directed to be parallel to one another. A mount is displaceable along the parallel bundles of rays, the sample material and a collecting optical member being fastened on the mount at a distance from one another equal to the focal length of this optical member.

7 Claims, 1 Drawing Figure

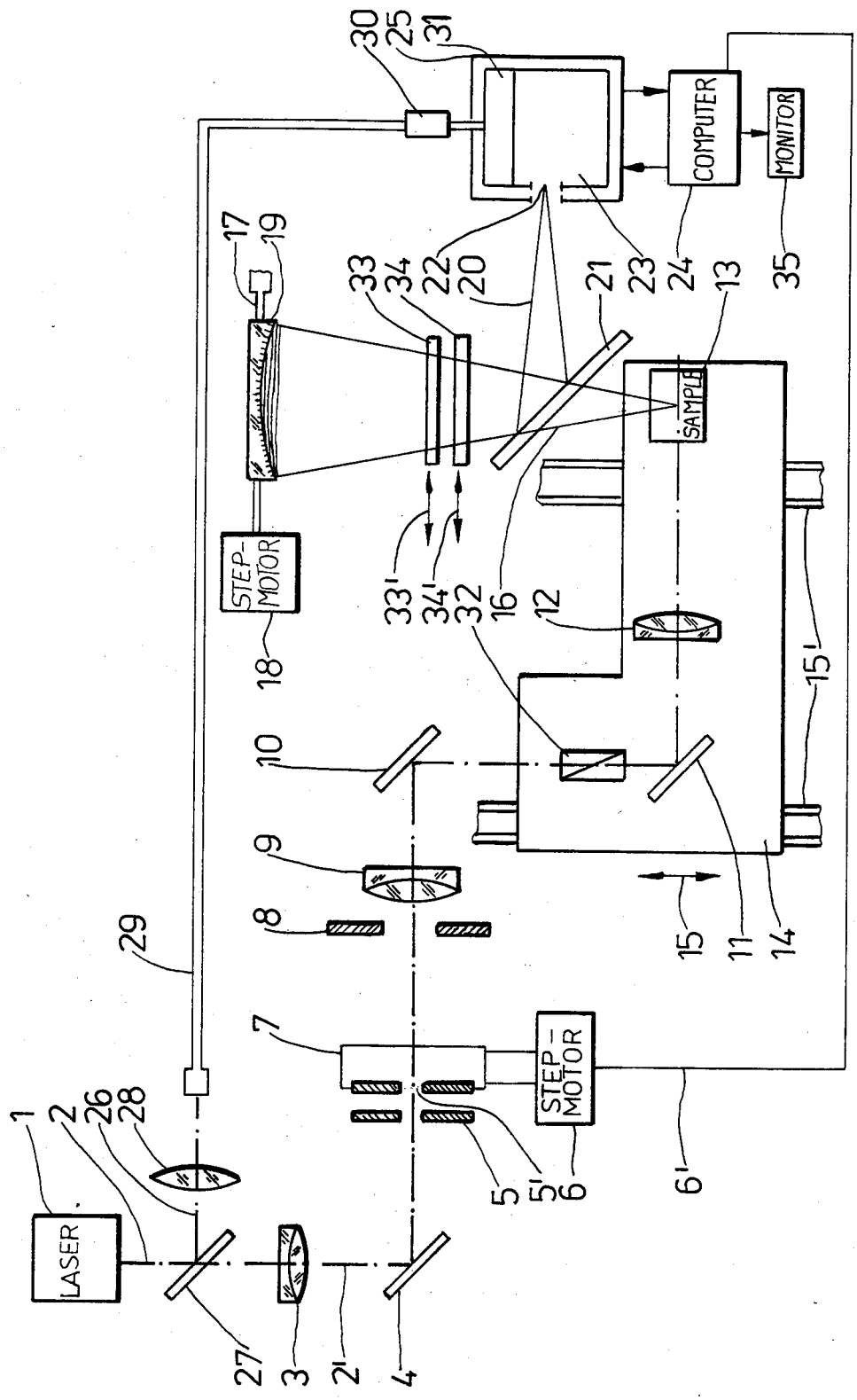

LASER SPECTRAL FLUOROMETER

The invention relates to a laser spectral fluorometer in which the luminescence light emitted by a sample material is investigated in a qualitative or quantitative analysis.

In time resolved luminescence spectroscopy a sample material is excited for a short time with light and the resulting luminescence radiation is measured time resolved. Since the stray light appears synchronously with the excitation light, the luminescence radiation, however, depending on the sample material, being delayed, more or less significantly, this method is very suitable for suppressing the stray light. In addition thereto, the time-resolved measurement of the luminescence radiation yields informations on a luminophore in its unbound medium. This is of increasing importance in biology, food science, pharmacy and medical science. The life time of the luminescence of a molecule is very often a more precise measure for the changes in the molecular environment than the intensity of emission since it can be absolutely evaluated. In the absence of bimolecular processes it is independent of the concentration of the luminophore. Pulsed lasers are more and more used as light sources, which have a high power output, for the time resolved luminescence measurement. An adjustable stopping dawn of the laser light over several orders of magnitude is necessary to enable operation in the linear range of a sample or to eliminate a transgression of the dynamic range of the measuring system. To this end a plurality of filters is required to cover a wide range of intensities. This, however, only permits a stepped stopping dawn. It is very expensive to obtain an automated control of the light power over a wide spectral range using these means. The focusing of excitation laser light into the sample yields a thin linear range in the sample which emits a luminescence light.

The luminescence light which is generally measured at an angle of 90° relative to the excitation radiation is focused with a great relative aperture into the entry slit of an emission monochromator to obtain a high detection efficiency. Provided that different cuvettes are used, or filters inserted into the luminescence path of radiation or a cryostat is employed for tempering the sample, the optical path length to the entry slit will vary. The position of the focus in the radiation exit will vary when the grating of the monochromator is used in the zero order in addition to its first order, as it is suitable when a luminescence of low intensity has to be detected. Though the change of the grating for an imaging reflector is dispensed with, the different focal widths have to be balanced.

Accordingly, a precise focusing of the luminescence light into the entry slit of the emission monochromator requires matched optical imaging which is expensive. When the sample is located in the entrance opening of the emission monochromator so that the narrow linearly excited range of the sample represents the entry slit, a variation of the optical path length to the grating or to the prism will also occur which, in turn, results in a defocusing in the exit slit when the means mentioned hereinbefore are used so that losses in spectral resolution are involved.

Furthermore, an expensive variation of the path of rays and of the imaging relations is necessary when measuring highly absorbing samples, since the excitation of the sample and the measurement of the luminescence radiation have to be carried out from the same side of the sample, and also in this case the optical path length to the entry slit of the monochromator varies.

It is an object of the present invention to obviate the above disadvantages.

It is a further object of the present invention to increase the sensitivity and the spectral resolution of an arrangement for measuring the luminescence radiation of diverse sample materials under different measuring conditions at considerably low expenditures.

It is still a further object of the present invention to provide a laser spectral fluorometer having optical imaging conditions suitable for different optical paths for the luminescence light emitted by a sample material at a variable output in the spectral range of the excitation source. These and other objects of the invention are realised in a laser spectral fluorometer in which a sample material is excited by a focused excitation bundle of rays originating from a laser light source to emit a secondary bundle of rays fed into an emission monochromator or spectrograph with a subsequent detector system, characterized in that subsequent to the laser light source a first optical member is provided in the excitation bundle of rays which produces an image point in a slit which is adjustably variable from open to shut, the variation being measurable, and a second optical collective member following the slit at a distance of its focal length. The sample material and a third optical collective member arranged in the excitation bundle of rays are secured to a common mount at a mutual distance from one another of the focal length of the third optical collective member. It is essential for the invention that at least portions of the excitation bundle of radiation and of the central beam of the secondary beam are parallel to one another, the common mount being displaceable along the parallel portions. Advantageously, the adjustable variable slit is constituted of a combination of a slit aperture and a concentrical aperture and permits a full blanking off and a stepped stopping dawn of the excitation bundle of rays.

The optical path length required for a minimum defocussing in an exit opening of the monochromator or spectrograph is adjusted by displacing the common mount and, hence, of the sample and the associated third optical collective member along the parallel portions of the excitation bundle of rays and the central beam of the secondary radiation.

The displacement of the common mount is executed until a sharp image is obtained of the excited sample range which serves as an entrance slit. The solution according to the invention permits to use the laser spectral fluorometer for measuring the luminescence in the zero and first order,
measuring the luminescence from the sample volume, or by a reflected light measurement,
measuring the luminescence by insertion of order filters, and
measuring the luminescence by tempering of the sample under use of a cryostat.

In order that the invention is more readily understood reference is made to the accompanying drawing which illustrates diagrammatically and by way of example one embodiment thereof and wherein the FIGURE is schematic view of a laser spectral fluorometer arrangement according to the invention.

A laser radiation 2 generated by a dyestuff laser 1 which is a pulsed laser tunable over a wide spectral range impinges upon a collective lens 3 which, in the present example, is an achromatic lens system 3, and is directed by a deviating reflector 4 through a concentrical aperture 5 upon a variable slit 7 which is operated by a step-motor 6. The variable slit 7 is followed, in the propagation direction of the laser radiation 2 (2'), by an aperture 8 and an achromatic lens system 9 which is remote from the slit 7 at the distance of its focal length, that is, the slit 7 is located in the focal plane of the achromat 9. The laser radiation 2 rendered parallel by the achromat 9 is directed via the deviating reflectors 10 and 11 and an achromatic lens system 12 into a sample 13 which is arranged in a focus of the achromat 12. The deviating reflector 11, the lens system 12 and the sample 13 are arranged on a common mount 14 which is displaceable on slides 15' in directions indicated by a double arrow 15. A luminescence radiation 16 emitted by the sample 13 and to be measured at an angle of 90° relative to the excitation laser beam 2 is directed upon a holographic concave grating 19 rotatably seated about an axis 17 and driven by a step motor 18, of an emission monochromator. The emission monochromator substantially comprises the entry slit 13, the holographic grating 19 and an exit slit 22, which simultaneously is an entry slit of a streak camera 25. The locus of excitation of the sample 13 forms the entry slit of the emission monochromator. The grating 19 disperses the bundle of rays 20 into a plurality of wavelengths and focuses the latter via a deviating reflector 21 into the entry slit 22 of an electron optical image converter 23. The luminescences radiation 16 is assumed to lie in the drawing plane (in fact, it is a cone shaped radiation) and the deviating reflector 21 does not affect the same. The luminescence radiation 16 is dispersed at the grating 19 into radiation 20 which lies in a plane which includes an angle with the drawing plane.

In the DD-PS 157985, the image converter 23 is disclosed in more detail, it is a component of the streak camera 25 which is coupled to a computer 24 and serves to control the measuring procedure, the data acquisition and processing, and includes int.al. an A/D converter.

Since the image converter 23 only has to measure synchronously to the impinging luminescence radiation 20, a synchronisation is obtained in that a deviating reflector 27 splits the laser 1 output into the beams 2' and 26 which is fed into a light cable 29 by a lens 28. The light cable 29 is connected to an optoelectronic detector 30 which controls the scanning generator 31 of the image converter 23.

A Glan-Thompson polariser 32 is arranged for insertion into the laser beam 2 between the deviating reflectors 10 and 11 for depolarisation measurements, and an analyzer 33 for adjustable orientation between the sample 13 and the concave grating 19.

Furthermore, an order filter 34 is arranged for insertion between the sample 13 and the concave grating 19. For measurement of the emission spectra the concave grating 19 is rotated about the axis 17.

—When the order filter 34 and the analyzer 33 are arranged by respective displacements indicated by the double arrow 33' and 34', respectively, in the luminescence path of rays 16 or when a cryostat is employed for the sample material 13 then the path length to the concave grating 19 has to be varied to obtain a sharp spectrum. A significantly greater variation also occurs at a variation of the order of the concave grating 19 used for the measurement. The carrier 14, therefore, has to be displaced in one of the directions indicated by the double arrow 15 until the spectrum is focused upon a not shown phototube of the image converter 23. This can be observed on a monitor 35. Strongly absorbing samples are arranged relative to the excitation laser beam 2 at such an angle that the light reflected on the sample surface does not pass the grating 19 and the luminescence emitted from the irradiated side of the sample can be measured. The position of the sample is so selected that the range of excitation in the sample material 13 lies in the optical axis of the concave grating 19. A variation of the object path length can also be counteracted by displacement of the carrier 14 in a respective direction indicated by the double arrow 15.

In operation, the laser 1 emits a pulsed laser radiation 2 which is split by the partially transmissive, partially reflective reflector 27 into the excitation radiation 2' and into a trigger radiation 26. The excitation radiation 2' is directed via the lens 3, the deviating reflector 4, the slit 5 and the variable slit 7, the aperture 8, the lens 9, the deviating reflectors 10 and 11 to the lens 12 which focuses the excitation radiation 2' into the sample material 13 which is thus excited to emit a luminescence radiation 16. The latter impinges upon the holographic grating 19 which has an axis of rotation 17. The latter lies in the drawing plane and, hence, the luminescence radiation 16 which is dispersed into a radiation of individual wavelengths 20 is directed to the deviating reflector 21 in a plane which includes an angle with the drawing plane. From the reflector 21 the radiation 20 is directed into the exit slit 22 of the monochromator which at the same time is the entry slit of the photocathode of the image converter 23.

At the same time, the triggering beam 26 is focused into the entry face of the light cable 29 which is connected to the streak camera 25 via the opto-electrical detector 30 which, in turn, converts the incoming radiation 26 into electrical signals. The latter start operation of the saw tooth generator 31 of the image converter 23, at the same time the radiation 20 impinges upon the entry slit 22 of the image converter 23, which produces an electron cloud in response to the arriving electromagnetic radiation 20. The electron cloud is spread by electrodes to which the saw tooth generator 31 voltage is applied. The spread electron cloud impinges upon a subsequent silicon target which is scanned by a vidicon. Provided that the energy transmitted by the radiation 20 transgresses the dynamic range of the streak camera 25 the A/D converter becomes inoperative and feeds a respective signal to the computer 24 which controls the step-motor 6 via a line 6'. The step-motor 6 reduces the slit width of the variable slit 7 until the dynamic range of the streak camera 25 is reached again.

The individual components mentioned in connection with the streak camera 25 are not shown in the drawing, specifically, they are disclosed, for example, in the DD-PS No. 157 985 in more detail.

In the event that the grating 19 is rotated about the axis 17 by operation of the step-motor 18, or when the order filter 34 and the analyzer 33 are inserted into the luminescence radiation 16 the object focal length has to be varied in order to obtain a focused image of the respective wavelength in the entry slit 22. This is achieved in that the carrier 14 is displaced in a respective direction indicated by the double arrow 15, until the spectrum on the cathode tube of the image converter 23 transmitted by the radiation 20 is sharp, which is observed on the monitor 35. The displacement of the carrier 14 is performed by not shown displacement means on the slides 15'.

The invention is not restricted to the above embodiment. It is feasible to use a fast secondary electron multiplier combined with suitable computing and control means instead of the streak camera. Furthermore, it is feasible to employ imaging reflectors for the members 9, 10 and 11, 12.

The laser 1 can be constituted of a combination of a $N_2$-laser which pumps a dyestuff laser.

We claim:

1. A laser spectral fluorometer for analyzing a sample material, comprising
   a laser radiation source for emitting a pulsed laser radiation over a given spectral range,
   a first optical member,
   at least a first slit,
   a second optical member having an object side focus,
      said first optical member producing a narrow diameter portion of said laser radiation in said first slit,
      said first slit being variable within two end positions, the one end position being fully open, the other end position being closed,
      said first slit being arranged in said object side focus of said second optical member,
   means for varying said first slit,
      said second optical member imaging said laser radiation at infinity,
   at least a first deviating member, a third optical member, and a sample material to be analyzed,
   a displaceable base,
      said first deviating member, said third optical member, and said sample material being commonly mounted on said base subsequently in said laser radiation,
      said first deviating member directing said laser radiation from said second optical member to said third optical member,
      said first deviating member folding said laser radiation by 90°,
      said third optical member focusing said laser radiation into said sample material for exciting the latter,
   a luminescence radiation thereby being emitted by the excited sample material substantially at right angles to said laser radiation, impinging upon said sample material, and substantially in parallel to at least a portion of said laser radiation before said first deviating member,
   an emission monochromator, in turn, comprising a concave reflective grating rotatably seated about a substantially horizontal axis,
      said concave reflective grating having an image side focus, and being arranged in opposition to said sample material in said luminescence radiation,
      said concave reflective grating dispersing said luminescence radiation into a dispersed wavelengths radiation,
   a reflector,
   an evaluation unit having an entry slit,
      said reflector directing said dispersed wavelengths radiation into said entry slit,
      said image side focus being located in said entry slit,
   means for displacing said base in a plane defined by said laser radiation and said luminescence radiation, substantially along the latter,
      said means for displacing said base adjusting said image side focus in said entry slit.

2. A laser spectral fluorometer as claimed in claim 1, wherein said plane and said dispersed wavelengths radiation include an angle.

3. A laser spectral fluorometer as claimed in claim 2, wherein a beam spitting means is provided in said laser radiation between said laser light source and said first optical member for splitting a triggering beam from said laser radiation for triggering operation of said evaluation unit only for the period of time a laser pulse is transmitted by said laser radiation.

4. A laser spectral fluorometer as claimed in claim 3, wherein said means for varying said first slit is a servomotor which is controlled via a connection to said evaluation unit by the latter.

5. A laser spectral fluorometer as claimed in claim 4, wherein said evaluation unit comprises an image conversion member, computing means, and a display means for monitoring the image side focus in said entry slit of said evaluation unit.

6. A laser spectral fluorometer as claimed in claim 5, wherein a second optical deviating member is inserted into the laser radiation between said first optical member and said first slit, and a third optical deviating member is between said second optical member and said first optical deviating member.

7. A laser spectral fluorometer as claimed in claim 6, wherein order members are provided to said luminescence radiation.

* * * * *